(12) United States Patent
Chang et al.

(10) Patent No.: US 9,375,447 B2
(45) Date of Patent: Jun. 28, 2016

(54) MODIFIED HYALURONAN AND USES THEREOF IN CANCER TREATMENT

(71) Applicant: National Cheng Kung University, Tainan (TW)

(72) Inventors: Nan-Shan Chang, Owega, NY (US); Wan-Pei Su, Nantou (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/826,952

(22) Filed: Mar. 14, 2013

(65) Prior Publication Data

US 2014/0271620 A1 Sep. 18, 2014

(51) Int. Cl.
  *A61K 31/738* (2006.01)
  *A61K 39/395* (2006.01)
  *C08B 37/08* (2006.01)
  *A61K 31/728* (2006.01)
  *C07K 16/44* (2006.01)

(52) U.S. Cl.
  CPC ............. *A61K 31/738* (2013.01); *A61K 31/728* (2013.01); *A61K 39/3955* (2013.01); *C07K 16/44* (2013.01); *C08B 37/0072* (2013.01)

(58) Field of Classification Search
  CPC ..... A61K 31/728; A61K 47/26; A61K 31/70; C08B 37/0072
  See application file for complete search history.

(56) References Cited

U.S. PATENT DOCUMENTS

| 5,902,795 | A | 5/1999 | Toole et al. |
| 2005/0281880 | A1 | 12/2005 | Wang |
| 2006/0178342 | A1* | 8/2006 | Brown et al. ................... 514/54 |
| 2007/0202491 | A1 | 8/2007 | Hendrix et al. |

FOREIGN PATENT DOCUMENTS

| WO | WO 97/40841 | * 11/1997 | ........... A61K 31/715 |

OTHER PUBLICATIONS

Luo et al. (Biomacromolecules, 1: 208-218, 2000).*
Chang et al., Hyaluronic acid-complement interactions—I.Reversible heat-induced anticomplementary activity. Mol Immunol. Apr. 1985;22(4):391-7.
Chang et al., Hyaluronic acid-complement interactions—II. Role of divalent cations and gelatin. Mol Immunol. Aug. 1985;22(8):843-8.
Hsu et al., Transforming growth factor beta1 signaling via interaction with cell surface Hyal-2 and recruitment of WWOX/WOX1. J Biol Chem. Jun. 5, 2009;284(23):16049-59. doi: 10.1074/jbc.M806688200. Epub Apr. 14, 2009.
Kubo et al., Depolymerization of hyaluronan by sonication. Glycoconj J. Dec. 1993;10(6):435-9.
Ossipov, Nanostructured hyaluronic acid-based materials for active delivery to cancer. Expert Opin Drug Deliv. Jun. 2010;7(6):681-703. doi:10.1517/17425241003730399.

* cited by examiner

*Primary Examiner* — Brad Duffy
*Assistant Examiner* — Nelson B Moseley, II
(74) *Attorney, Agent, or Firm* — Wolf, Greenfield & Sacks, P.C.

(57) ABSTRACT

Uses of depolymerized hyaluronan (e.g., prepared by sonicating high molecular weight hyaluronan such as naturally-occurring hyaluronan) or anti-Hyal-2 antibody in cancer treatment. Also described herein are methods for preparing depolymerized and crosslinked hyaluronan by sonication and the hyaluronan composition thus obtained.

12 Claims, 7 Drawing Sheets

SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1

```
Cys Pro Asp Val Glu Val Ala Arg Asn Asp Gln Leu Ala Trp Leu
1               5                   10                  15
```

<210> SEQ ID NO 2
<211> LENGTH: 473
<212> TYPE: PRT
<213> ORGANISM: Homo sapiens

<400> SEQUENCE: 2

```
Met Arg Ala Gly Pro Gly Pro Thr Val Thr Leu Ala Leu Val Leu Ala
1               5                   10                  15

Val Ser Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300
```

-continued

```
Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
            325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
        370                 375                 380

Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
            405                 410                 415

Asp Ile Asp His Leu Gln Thr His Phe Arg Cys Gln Cys Tyr Leu Gly
            420                 425                 430

Trp Ser Gly Glu Gln Cys Gln Trp Asp His Arg Gln Ala Ala Gly Gly
            435                 440                 445

Ala Ser Glu Ala Trp Ala Gly Ser His Leu Thr Ser Leu Leu Ala Leu
    450                 455                 460

Ala Ala Leu Ala Phe Thr Trp Thr Leu
465                 470
```

MODIFIED HYALURONAN AND USES THEREOF IN CANCER TREATMENT

BACKGROUND OF THE INVENTION

Hyaluronan, also known as hyaluronic acid (HA) or hyaluronate, is a non-sulfated, anionic glycosaminoglycan distributed in various tissues, e.g., connective, epithelial, and neural tissues. HA is a polymer of disaccharides composed of D-glucuronic acid and D-N-acetylglucosamine, which are linked via alternating β1,4- and β1,3-glycosidic bonds. HA has been found to play various physiological roles in the intercellular matrix, including cell migration, proliferation, and differentiation, tissue repair and hydrodynamics, and immune regulation.

Naturally-occurring HA often contains 10,000 or more disaccharide units, the molecular weight of which can reach 4 million daltons or higher. Such high molecular weight HA molecules can be degraded via enzymatic, chemical, or physical methods to produce depolymerized HA products.

High molecular weight HA (e.g., native HA) has anti-angiogenic, anti-inflammatory, and immunosuppressive effects. By contrary, small HA fragments can induce the release of inflammatory chemokine, stimulate CD44 cleavage, increase angiogenesis, and promote tumor cell migration.

In humans, HA is degraded by hyaluronidases, which include six members, e.g., hyaluronidases 1-4 (Hyal 1-Hyal 4) and hyaluronidase PH-20. Among them, Hyal-2 is an anchor protein located on the outer cell membrane via the glycosylphosphatidyl-inositol (GPI) linkage. It was found that HAYL-2 is a receptor of transforming growth factor beta 1 (TGF-β1). Hsu et al., J. Biol. Chem., 284:16049-16059; 2009.

SUMMARY OF THE INVENTION

The present disclosure is based on the unexpected discoveries that depolymerized and crosslinked hyaluronan, which can be prepared by sonicating high molecular weight HA (e.g., native HA), or anti-Hyal-2 antibody significantly suppressed cancer cell growth in mouse models, while high molecular weight native HA did not show this anti-cancer effect.

Accordingly, one aspect of the present disclosure features a method for suppressing cancer cell growth comprising contacting cancer cells (e.g., breast cancer cells, melanoma cells, skin basal cell carcinoma cells, prostate cancer cells, lung cancer cells, glioblastoma cells, or neuroblastoma cells) with a composition comprising depolymerized hyaluronan, which can comprise inter-chain covalent crosslinks. In some embodiments, at least about 90% of the depolymerized hyaluronan has a molecular weight ranging from about 100-500 kDa.

Another aspect of the present disclosure features a method for treating cancer (e.g., breast cancer, melanoma, skin basal cell carcinoma, prostate cancer, lung cancer, glioblastoma, or neuroblastoma). The method comprises administering to a subject in need thereof the depolymerized HA as described above. In some examples, the subject in need of the treatment is a subject (e.g., a human patient) diagnosed with cancer. In other examples, the subject is a subject (e.g., s human patient) suspected of having or at risk for cancer.

In any of the methods described herein, the depolymerized hyaluronan can contain inter-chain crosslinks at a level equal to or greater than about 25%.

In some embodiments, the depolymerized hyaluronan used in any of the methods described herein can be prepared by sonication of high molecular weight hyaluronan (e.g., native hyaluronan). The sonication can be carried out at about 20-80 kHz (e.g., 50-60 kHz) for about 3-6 hours. Alternatively or in addition, it can be carried out under a temperature ranging from about 50-80° C. (e.g., 65 to 70° C.).

In addition, the present disclosure provides a method for preparing depolymerized and crosslinked hyaluronan, comprising sonicating high molecular weight hyaluronan at about 20-80 kHz for about 3-6 hours, and optionally under a temperature ranging from about 50-80° C. (e.g., 65 to 70° C.). Any composition comprising depolymerized and crosslinked hyaluronan prepared by the just-described method is also within the scope of this disclosure.

In yet another aspect, the present disclosure provides a method for treating cancer, comprising administering to a subject in need thereof an effective amount of an antibody capable of binding to hyaluronidase-2 (Hyal-2), e.g., Hyal-2 expressed on cell surfaces. In some embodiments, the antibody binds to CPDVEVARNDQLAWL(SEQ ID NO:1) or a fragment thereof. The anti-Hyal-2 antibody used in the method described herein can be a full-length antibody or an antigen-binding fragment thereof. Alternatively, the antibody can be a human antibody or a humanized antibody.

In some embodiments, the subject in need of the antibody treatment is a subject (e.g., a human patient) diagnosed with cancer. In other embodiments, the subject (e.g., a human patient) is suspected of having cancer or is at risk for developing cancer. Examples of cancers to be treated by this method include, but are not limited to, melanoma, basal cell carcinoma, skin basal cell carcinoma, prostate cancer, lung cancer, glioblastoma, and neuroblastoma.

Also within the scope of this disclosure are compositions, such as pharmaceutical compositions, for use in treating cancer or suppressing cancer cell growth, the composition comprising depolymerized hyaluronan or anti-Hyal-2 antibody as described herein, and uses of such anti-cancer agent in manufacturing a medicament for treating cancer, including any of the cancers described herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION OF THE INVENTION

The present disclosure is based on the unexpected discoveries that depolymerized HA (having molecular weight in a specific range) and anti-Hyal-2 antibodies suppressed cancer cell growth in animal models. Without being bound by theory, either the depolymerized HA or the anti-Hyal-2 antibody might bind to Hyal-2, a cell membrane anchor protein, on certain types of immune cells, leading to the desired anti-cancer effect.

Accordingly, described herein are methods of treating cancer using depolymerized HA, anti-Hyal-2 antibody, or a combination thereof, pharmaceutical compositions comprising one or more of the anti-cancer agent, methods for preparing the depolymerized HA, and compositions produced by such preparation methods.

Depolymerized HA

Naturally-occurring hyaluronan (HA) or native HA found in various tissues contains 10,000 or more disaccharide units and has a molecular weight greater than 4 million Dalton (the average MW of a disaccharide unit of HA is about 400 daltons). In diluted solution, HA forms random coils with some degree of local conformational ordering, while in concentrated solution, HA forms a meshwork-like network via intensive inter-chain association and molecular overlapping. Chang et al., *Mol. Immunol.* 22(8):843-848; 1985; and Chang et al., *Mol. Immunol.* 22(4):391-397; 1985.

High molecular weight HA (e.g., MW over 4 million kDa) was found to promote cancer cell growth. Similarly, small HA fragment (e.g., MW less than 100 kDa) can increase angiogenesis and promote cancel cell growth via stimulation of CD44 cleavage. Surprisingly, results from the present study showed that HA with certain levels of degradation and/or crosslinking significantly suppressed cancer cell growth in mouse cancer models, suggesting that such depolymerized HA is effective in treating cancer.

The depolymerized hyaluronan described herein has a molecular weight much less than native HA but greater than small HA fragments noted above. In some embodiments, at least 80% (e.g., 85%, 90%, 92%, 95%, 97%, 98%, 99%, or over) of the depolymerized HA for use in cancer treatment as described herein has a molecular weight ranging from 100-500 kDa (e.g., 150 kDa-450 kDa; 200 kDa-400 kDa, 200 kDa-500 kDa, 300 kDa-500 kDa, 400 kDa-500 kDa, 100 kDa-200 kDa, 100 kDa-300 kDa, or 100 kDa-400 kDa).

Preferably, the depolymerized HA described herein has a high degree of inter-chain covalent crosslinks, which might contribute to the anti-cancer effect of the depolymerized HA. An inter-chain covalent crosslink refers to a covalent bond formed between two distinct HA molecules. In some embodiments, the level of inter-chain covalent crosslinks in the depolymerized HA is at least 25%, i.e., at least 25% of the HA molecule in the total population contain at least one covalent crosslink with another HA molecule. In other embodiments, the depolymerized HA has an inter-chain covalent crosslink level of at least 30%, e.g., 40%, 50%, 60%, 70%, 80%, or 90%.

The depolymerized HA described herein may also contain conformational alterations as compared to native HA. In some embodiments, at least 50% (e.g., 60%, 70%, 80%, 90%, 95%, or over) of the depolymerized HA can have N-acetylglucosamine at the reducing end and/or glucuronic acid at the non-reducing end. In one example, at least 85% of the reducing termini in the depolymerized HA is N-acetylglucosamine and/or at least 95% of the non-reducing termini is glucuronic acid.

The depolymerized HA described herein can be prepared by any suitable methods known in the art. In some embodiments, the depolymerized HA is prepared by sonication. For example, high molecular weight HA (e.g., MW over 1, 2, 3, or 4 million daltons) can be sonicated under suitable conditions (e.g., frequency, duration, and temperature) to degrade HA but not to over degrade HA, thereby producing depolymerized HA having the desired anti-cancer effect. In one example, the sonication process can be performed under one or more of the following conditions:

Frequency: 20-100 kHz, e.g., 20-80 kHz, 40-80 kHz, 50-70 kHz, 60-70 kHz, or 60-75 kHz.

Duration: 2-8 hr., e.g., 3-6 hr, 2-7 hr, or 4-6 hr.

Temperature: 50-90° C., e.g., 50-90° C., 50-80° C., 60-80° C., 70-80° C., or 75-80° C.

Suitable sonication conditions for producing the desired depolymerized HA would be appreciated by skilled artisans and can be determined via routine practice. One example follows.

Native HA, which can either be isolated from tissues or obtained from a commercial vendor (for medical grade HA), can be sonicated under predetermined conditions. The resultant degraded HA can be examined to determine the MW range via routine technology (e.g., electrophoresis). The sonication condition can then be adjusted based on the results thus obtained. If a substantial portion of the degraded HA has a MW exceeding a predetermined value, e.g., 500 kDa, the sonication conditions can be adjusted, e.g., increase frequency, duration, and/or temperature, such that greater degradation can be achieved. On the other hand, if a substantial portion of the degraded HA has a MW lower than a predetermined value, e.g., 100 kDa, the sonication conditions can be adjusted to reduce the level of degradation.

In one example, the sonication process is carried out at about 53 kHz for about 3-6 hours under about 70° C.

The depolymerized HA obtained from the methods described above, having suitable features such as MW, inter-chain crosslinking level, and/or conformational alteration, can be investigated to confirm its anti-cancer effect via conventional methods, e.g., those described in the examples below.

Any depolymerized HA produced by any of the preparation method described above and compositions (e.g., pharmaceutical compositions) containing such are also within the scope of the present disclosure.

Anti-HYAL-2 Antibody

Hyaluronidase-2, is an enzyme that degrades hyaluronan in vivo. As an example, the amino acid sequence of human Hyal-2 is provided below (SEQ ID NO:2):

```
mragqgptvt  lalvlavswa  melkptappi  ftgrpfvvaw  dvptqdchpr  lkvpldlnaf
dvqaspnegf  vnqnitifyr  drlglyprfa  sagrsvnggv  pqnvslwahr  kmlqkrvehy
irtgesagla  vidwedwrpv  wvrnwqdkdv  yrrlsrqlva  srhpdwppdr  ivkqaqyefe
faaqqfmlet  lryvkavrpr  hlwgfylfpd  cynhdyvqnw  esytgrcpdv  evarndqlaw
lwaestalfp  svyldetlas  srhgrnfvsf  rvqealrvar  thhanhalpv  yvftrptysr
rlthlsemdl  istigesaal  gaagvilwgd  agyttstetc  qylkdyltrl  lvpyvvnvsw
atqycsraqc  hghgrcvrrn  psastflhls  tnsfrlvpgh  apgepqlrpv  gelswadidh
lqthfrcqcy  lgwsgeqcqw  dhrqaaggas  eawagshlts  llalaalaft  wtl
```

(i) Antibodies

The antibodies described herein for use in the cancer treatment also described herein are capable of binding to a hyaluronidase-2, such as human Hyal-2. For example, the antibody can bind to the regions in an Hyal-2 that corresponds to 227-241 in SEQ ID NO:2. In some embodiments, the antibody binds to CPDVEVARNDQLAWL (SEQ ID NO:1) or a fragment thereof. Such a fragment include at least 4 consecutive amino acid residues within SEQ ID NO:2. In some examples, the antibody bind to a fragment of SEQ ID NO:2 that has one or more deletions (e.g., deletions of 2, 3, 4, or 5 amino acid residues) at the N-terminus, the C-terminus, or both.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', $F(ab')_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in *Eur. J. Immunol.* (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a Hyal-2 or a fragment thereof (e.g., SEQ ID NO:1). An antibody that "specifically binds" to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other antigens or epitopes. For example, an antibody that specifically (or preferentially) binds to an Hyal-2 or an Hyal-2 epitope is an antibody that binds this antigen or epitope with greater affinity, avidity, more readily, and/or with greater duration than it binds to other antigens or epitopes (including other Hyal-2 epitopes). It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

The binding affinity of an anti-Hyal-2 antibody to Hyal-2 (e.g., human Hyal-2) as described herein, such as binding to membrane-bound human Hyal-2, can be less than any of about 100 nM, about 50 nM, about 10 nM, about 1 nM, about 500 pM, about 100 pM, or about 50 pM to any of about 2 pM. Binding affinity can be expressed as $K_D$ or dissociation constant, and an increased binding affinity corresponds to a decreased $K_D$. One way of determining binding affinity of antibodies to Hyal-2 is by measuring binding affinity of monofunctional Fab fragments of the antibody. To obtain monofunctional Fab fragments, an antibody (for example, IgG) can be cleaved with papain or expressed recombinantly. The affinity of an anti-Hyal-2 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human Hyal-2, and does not significantly bind an Hyal-2 from another mammalian species. In some embodiments, the antibody binds human Hyal-2 as well as one or more Hyal-2 from another mammalian species. In still other embodiments, the antibody can bind to a linear or conformational epitope of Hyal-2 such as human Hyal-2.

(ii) Antibody Preparation

Antibodies capable of binding to an Hyal-2 or a fragment thereof as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human Hyal-2) can be made by the conventional hybridoma technology. The full-length target antigen or a fragment thereof, optionally coupled to a carrier protein such as Keyhole limpet hemocyanin (KLH), can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-Hyal-2 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of binding to membrane-bound Hyal-2 and trigger the corresponding signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in modulating the signaling pathway mediated by Hyal-2. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., *Proc. Natl. Acad. Sci. USA*, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to Hyal-2 can be identified from the library following routine procedures. Positive clones can be subjected to further screening to identify those that trigger the signaling pathway mediated by Hyal-2.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the Hyal-2 polypeptide have been replaced (swapped) with sequences from a closely related, but antigenically distinct protein (such as another member of the neurotrophin protein family). By assessing binding of the antibody to the mutant Hyal-2, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Further, the anti-cancer effect of any anti-Hyal-2 antibodies thus prepared can be examined via routine technology and those described in the examples below.

Pharmaceutical Compositions

The depolymerized HA or the anti-Hyal-2 antibody can be mixed with a pharmaceutically acceptable carrier (excipient), including buffer, to form a pharmaceutical composition for use in suppressing cancer cell growth and treating cancer. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the anti-Hyal-2 antibody or the depolymerized HA. Such liposomes can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore sizes to yield liposomes with the desired diameter.

The active ingredients (e.g., anti-Hyal-2 antibody or depolymerized HA as described herein) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an anti-Hyal-2 antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Cancer Treatment

The term "cancer" as used herein refers to the physiological condition in mammals that is typically characterized by unregulated cell growth. Cancer as described herein can be benign and malignant cancers, metastatic cancers, adenomas, or adenocarcinomas. "Benign tumor" or "benign cancer" refers to a tumor that remains localized at the site of origin and does not have the capacity to infiltrate, invade, or metastasize to a distant site. "Malignant tumor" refers to a tumor that invades and damages other tissues around them.

The methods described herein can be applied for treating cancers of any type, including, but not limited to, squamous cell cancer, lung cancer (e.g., small-cell lung cancer, non-small cell lung cancer), gastric or stomach cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, prostate cancer, types of head and neck cancer, B-cell lymphoma (e.g., low grade/follicular non-Hodgkin's lymphoma); melanoma, mesothelioma, and multiple myeloma. Particular preferred are breast cancer, melanoma, basal cell carcinoma (e.g., skin basal cell carcinoma), prostate cancer, lung cancer, glioblastoma, and neuroblastoma.

To practice the methods for treating cancer as disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-Hyal-2 antibody or depolymerized HA as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer. A subject having cancer can be identified by routine medical examination, e.g., laboratory tests, CT scans, or ultrasounds. A subject suspected of having cancer might show one or more symptoms of the disorder, e.g., fever, extreme fatigue, unexplained weight loss, formation of blood clot in veins, feeling weak and dizzy, bloating, skin changes, difficulty swallowing, breast changes, bleeding, gnawing abdominal pain and depression, indigestion, mouth changes, pain, and/or persistent cough. A subject at risk for cancer can be a subject having one or more of the risk factors associated with that disorder. Risk factors associated with cancer include, but are not limited to, family history of cancer, tobacco and/or alcohol usage, smoking, viral infection (e.g., HBV, HCV, HPV, or EBV), excessive exposure to ionizing and/or ultraviolet radiation, estrogen, or carcinogen, genetic background (carrying cancer susceptibility genes such as BRCA-1 and BRCA-2).

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of cancer. Alternatively, sustained continuous release formulations of an anti-Hyal-2 antibody or depolymerized HA may be appropriate. Various formulations and devices for achieving sustained release are known in the art.

In one example, dosages for an anti-Hyal-2 antibody or depolymerized HA as described herein may be determined empirically in individuals who have been given one or more administration(s) of the active ingredient. Individuals are given incremental dosages of the agent. To assess efficacy of the antagonist, an indicator of cancer can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate cancer or a symptom thereof, or reduce the risk for cancer development. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

When depolymerized HA is used, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an anti-Hyal-2 antibody or depolymerized HA will depend on the specific agent employed, the type and severity of cancer, whether the therapeutic agent is administered for preventive or therapeutic purposes, previous therapy, the patient's clinical history and response to the agent, and the discretion of the attending physician. Typically the clinician will administer an anti-Hyal-2 antibody or depolymerized HA, until a dosage is reached that achieves the desired result. Administration of the therapeutic agent can be continuous or intermittent, depending, for example, upon the recipient's physiological condition, whether the purpose of the administration is therapeutic or prophylactic, and other factors known to skilled practitioners. The administration of the agent may be essentially continuous over a preselected period of time or may be in a series of spaced dose, e.g., either before, during, or after developing cancer.

As used herein, the term "treating" refers to the application or administration of a composition including one or more active agents to a subject, who has cancer, a symptom of cancer, or a predisposition toward the disease, with the purpose to cure, heal, alleviate, relieve, alter, remedy, ameliorate, improve, or affect the disorder, the symptom of the disease, or the predisposition toward the disease.

Alleviating cancer includes delaying the development or progression of the disease, or reducing disease severity. Alleviating the disease does not necessarily require curative results. As used therein, "delaying" the development of cancer means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

In some embodiments, the anti-Hyal-2 antibody or depolymerized HA described herein is administered to a subject in need of the treatment at an amount sufficient to suppress cancer cell growth in a patient by at least 20% (e.g., 30%, 40%, 50%, 60%, 70%, 80%, 90% or greater). In other embodiments, the therapeutic agent is administered to a patient (e.g., a cancer patient suspected of having cancer or at risk for developing cancer) to reduce the risk for cancer development, delay cancer onset, or suppress cancer progression.

Conventional methods, known to those of ordinary skill in the art of medicine, can be used to administer the pharmaceutical composition as described herein to the subject, depending upon the type of cancer to be treated or the site of the cancer. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethylormamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-HYLA-2 antibody or depolymerized HA is administered via site-specific or targeted local delivery techniques. Examples of site-specific or targeted local delivery techniques include various implantable depot sources of the therapeutic agent or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

When necessary, the therapeutic agents described herein can be co-used with other anti-cancer therapy, including chemotherapy (e.g., with one or more additional anti-cancer drugs), radiotherapy, and/or surgery. Treatment efficacy can be assessed by methods well-known in the art.

Kits for Use in Cancer Treatment

The present disclosure also provides kits for use in cancer treatment. Such kits can include one or more containers comprising an anti-Hyal-2 antibody (e.g., an antibody binding to human Hyal-2 or a fragment thereof such as SEQ ID NO:2) or depolymerized HA.

In some embodiments, the kit can comprise instructions for use in accordance with any of the methods described herein. The included instructions can comprise a description of administration of the therapeutic agent to treat, delay the onset, or alleviate cancer, or to reduce the risk for cancer development. The kit may further comprise a description of selecting an individual suitable for treatment based on identifying whether that individual has cancer or at risk for cancer. In still other embodiments, the instructions comprise a description of administering one or more of the therapeutic agents described herein to an individual suspected of having cancer or at risk of cancer.

The instructions relating to the use of an anti-Hyal-2 antibody or depolymerized HA generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset, alleviating cancer, and/or reducing the risk for cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

The kit described herein may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Preparation and Characterization of Deploymerzied Hyaluronic Acid (HA) by Sonication HA samples tested in this study were prepared as follows. Medical grade hyaluronan (high molecular weight) was obtained from Ginkgo-Trading Co., Ltd (Alhambra, Calif., USA). Two mg/ml of the hyaluronan (in sterile MilliQ water) was sonicated at 53 kHz for 3 and 6 hours at 70° C. using sonicator Soner 206H (Rocker Scientific Co) to produce sonicated HA samples HAson (3 hr) and HAson (6 hr), respectively. In addition, 2 mg/ml medical grade hyaluronan was treated by UV irradiation at 4 and 8 J/cm$^2$ using FB-UVXL-1000 (Fisher Scientific) to produce irradiated HA samples HAuv (4 J/cm$^2$) and HAuv (8 J/cm$^2$).

The HA samples prepared as described above were examined by agarose Gel electrophoresis as follows. 1% agarose gel was prepared in 1×TAE buffer (40 mM Tris, 82 mM acetic acid, and 8 mM EDTA, pH=7.9). HA samples containing 8 µg hyaluronan in 14 µl H$_2$O were mixed with 2 µl 2M sucrose in 1×TAE buffer (containing 0.02% bromophenol blue). Electrophoresis was carried out for 2.5 hours with a consistent voltage of 50 V. The agarose gel was then stained with 1% Alcian blue (in galactic acid, pH=2.5) for 1 hour under light protective cover, and destained overnight with 7% galactic acid.

Figure 1:
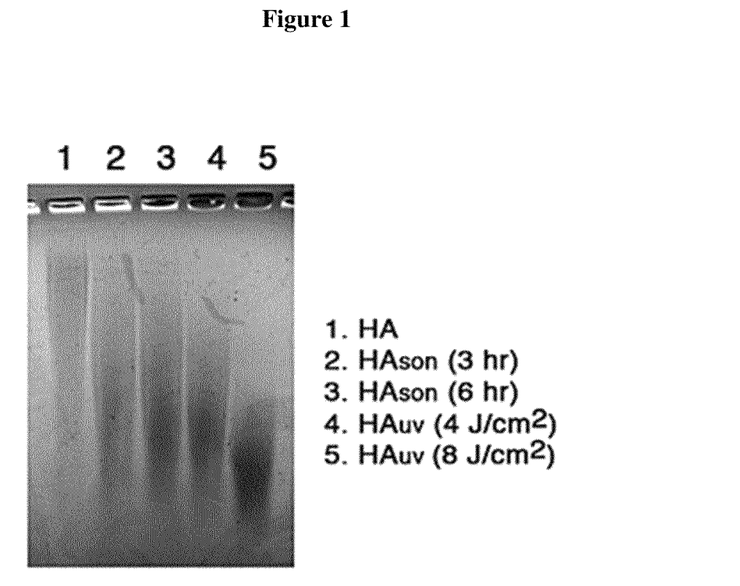
FIG. 1 is a photo showing native hyaluronic acid (HA), sonicated HA, and UV irradiated HA on an agarose gel after electrophoresis. Samples were stained with Alcian blue.

As shown in FIG. 1, both sonication and UV irradiation led to HA degradation, resulting in depolymerized HA, which has molecular weight lower than native HA. Moreover, UV irradiation causes HA degradation at a greater level than sonication, resulting in depolymerized HA having lower molecular weight than that produced by sonication.

Example 2

Sonicated Hyaluronic Acid (HA) Suppresses Melanoma Cell Growth

Figure 2:
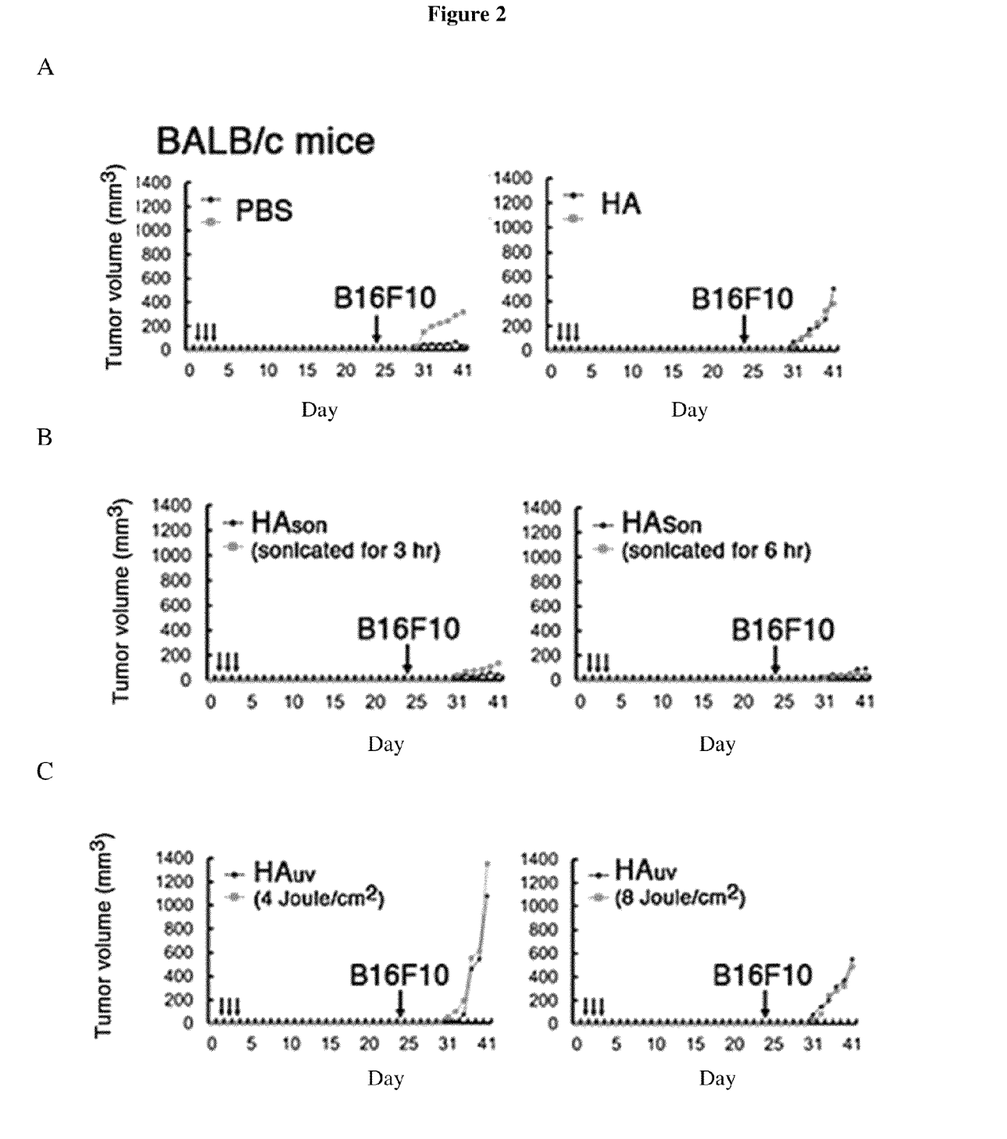
FIG. 2 is a graph showing the effect of native HA, sonicated HA, and UV irradiated HA in suppressing B16F10 melanoma cell growth in BALB/c mice. Panel A: mice treated with PBS or native HA. Panel B: mice treated with sonicated HA HAson (3 hr) and HAson (6 hr). Panel C: mice treated with UV irradiated HA HAuv (4 Joule/cm$^2$) and HAuv (8 Joule/cm$^2$).
Figure 3:
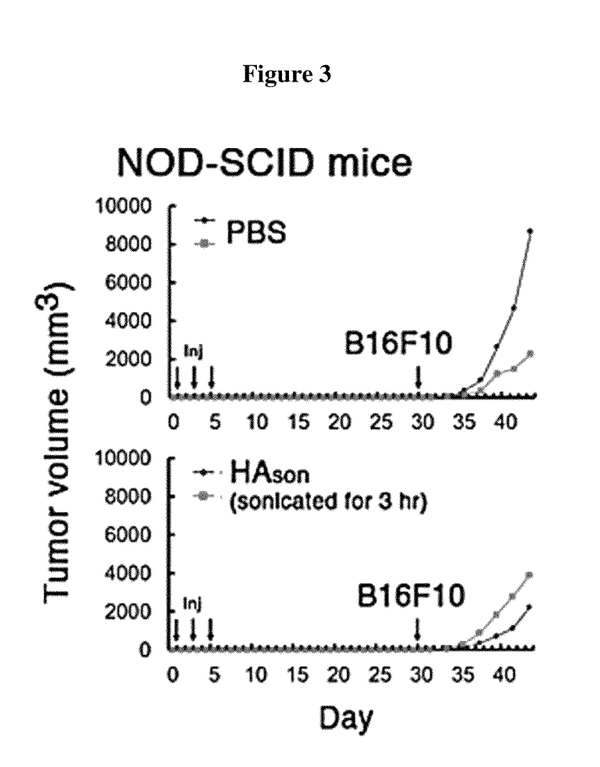
FIG. 3 is a graph showing the effect of sonicated HA in suppressing B16F10 melanoma cell growth in T and B cell-deficient NOD-SCID mice.

Immune competent BALB/c or T/B cell-deficient NOD-SCID mice were pretreated with 200 µg native HA (in 100 µl sterile MilliQ water), 200 µg sonicated HA, including HAson (3 hr) and HAson (6 hr) described in Example 1 above, and UV irradiated HA, including gHAuv (4 J/cm$^2$) and HAuv (8 J/cm$^2$) also described in Example 1 above via tail vein injections once every 2 days. PBS was used as a blank control. 19 days later, the mice were subcutaneously injected with melanoma B16F10 cells (2.5 million cells on both flanks as depicted in FIGS. 2 and 3, respectively. Tumor sizes were measured daily.

As shown in FIG. 2, Panel A native HA enhanced the growth of melanoma B16F10 cells in BALB/c mice. Surprisingly, sonicated HA effectively blocked B16F10 growth in the treated mice, while UV irradiated HA did not show this anti-cancer effect; instead, it promoted cancer cell growth. FIG. 2, Panels B and C.

Similarly, sonicated HA also significantly suppressed melanoma cell growth in NOD-SCID mice. See FIG. 3.

Example 3

Sonicated HA Suppresses Breast Cancer Cell Growth

Immune-deficient NOD-SCID mice were pretreated with 200 µg sonicated HA [HAson (3 hr) and HAson (6 hr) in 100 µl sterile MilliQ water] or MilliQ water as a blank control via tail vein injections once every 3 days. Three weeks later, the mice were subcutaneously injected with MDA-MB-231 breast cancer cells (2.5 million cells on both flanks. Tumor sizes were measured daily.

Figure 4:
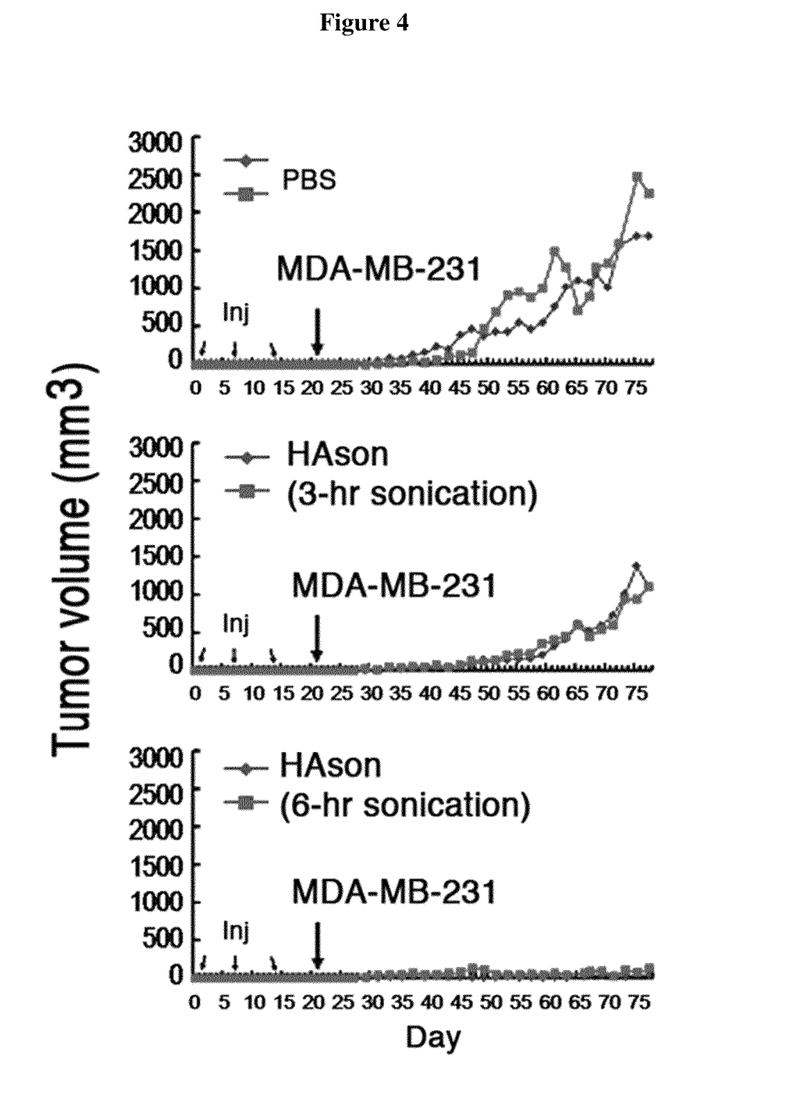
FIG. 4 is a graph showing the effect of sonicated HA in suppressing MDA-MB-231 breast cancer cell growth in NOD-SCID mice.

As shown in FIG. 4, both HAson (3 hr) and HAson (6 hr) sonicated HA samples dramatically inhibited the breast cancer growth, as compared to the control.

Example 4

Hyal-2 Antibody Suppresses Basal Cell Carcinoma Cell (BCC) Growth

An exemplary anti-Hyal-2 antibody was prepared as described in Hsu et al., J. Biol. Chem., 284(23):16049-16059, 2009. Briefly, a synthetic peptide of murine Hyal-2, NH2-CPDVEVARNDQLAWL-COOH (SEQ ID NO:1 corresponding to amino acids 227-241 of SEQ ID NO:2) was prepared following routine technology (Genemed Synthesis, San Antonio, Tex., USA). This region is a common domain in Hyal-2 of human, pig, and rat and was predicted to be a helical, surface-exposed segment, according to homology searching in the GenBank™ data base for the three-dimensional structure of the lyco_hydro_56 domain (or catalytic domain) in hyaluronidase.

SEQ ID NO:2 was used to immunize rabbits for producing antibodies capable of binding to the peptide, using an EZ antibody production and purification kit (Pierce), as described (Chang et al., J. Biol. Chem. 2001, 276, 3361-3370; Sze et al., J. Biol. Chem. 2004, 279, 30498-30506; Chang et al., J. Biol. Chem. 2003, 278, 9195-9202. Hyal-2 antisera containing polyclonal anti-Hyal-2 antibodies were collected.

Nude mice were injected with an aliquot of the Hyal-2 antiserum or normal rabbit serum (10 µl with 90 µl PBS) in 3 consecutive weeks. A week later, mice were subcutaneously injected with skin cancer BCC cells (2 million cells on flank). Tumor sizes were measured daily.

Figure 5:
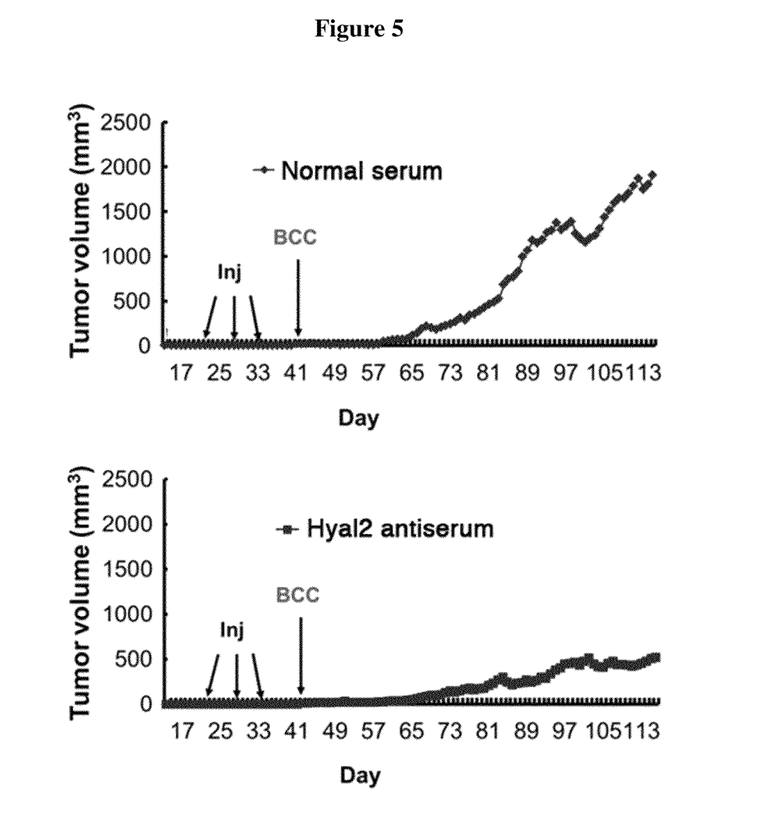
FIG. 5 is a graph showing the effect of anti-Hyal-2 antibody in suppressing basal cell carcinoma cell BCC growth in nude mice. Upper panel: normal serum as a control. Bottom panel: Hyal-2 antiserum.

As shown in FIG. 5, antiserum containing anti-Hyal-2 antibody, but not normal serum, blocked BCC growth.

Example 5

Hyal-2 Antibody Suppresses Melanoma Cell Growth

Immune competent BALB/c or T/B cell-deficient NOD-SCID mice were pretreated with the anti-Hyal-2 antibodies as described in Example 4 above (10 µl serum diluted with 9 µl PBS) via tail vein injections once every 3 days. Three weeks later, the mice were subcutaneously injected with skin melanoma B16F10 cells (2.5 million cells on both flanks). Tumor sizes were measured daily.

Figure 6:
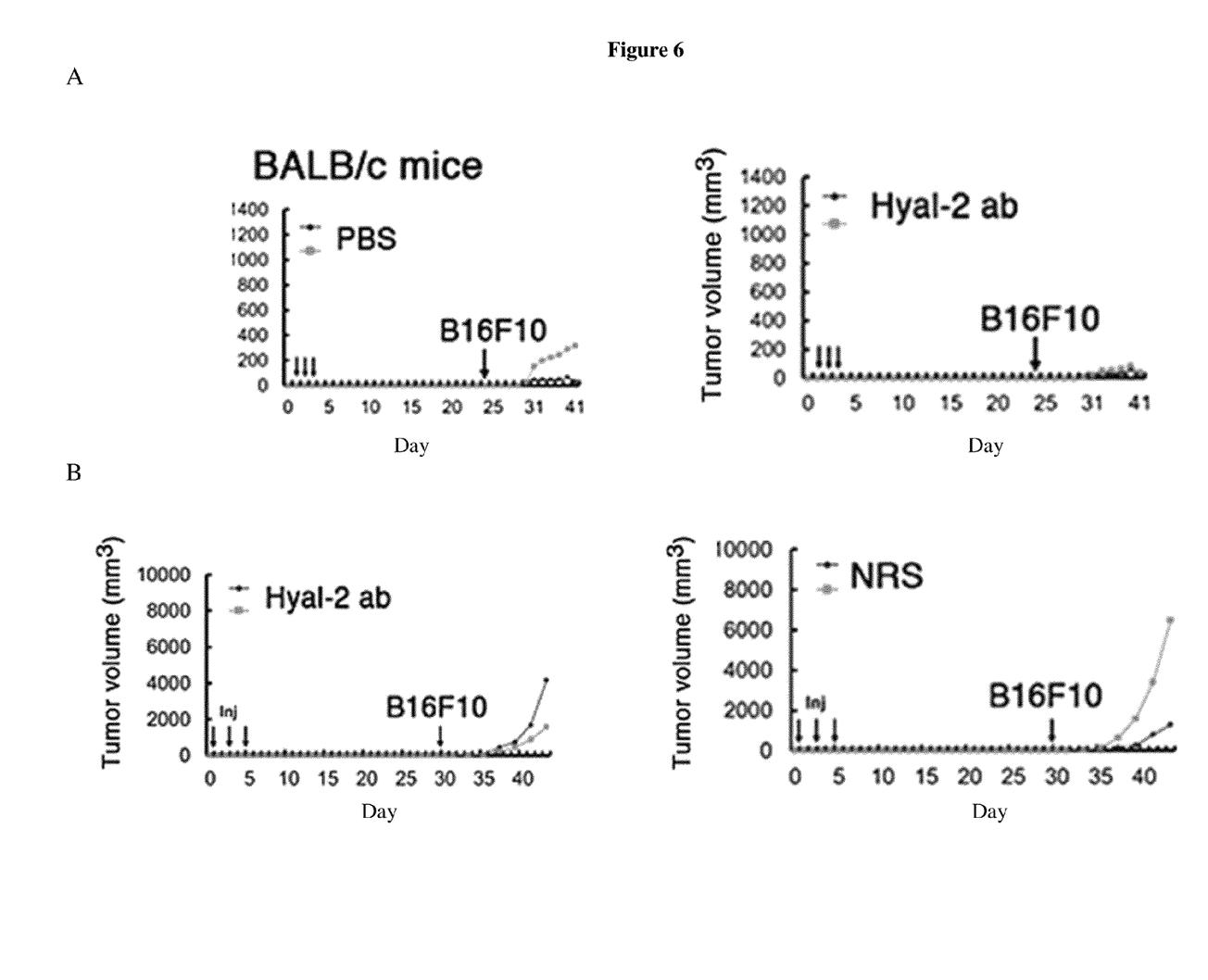
FIG. 6 is a graph showing the effect of anti-Hyal-2 antibody in suppressing B16F10 melanoma cell growth in BALB/c mice (panel A) and in NOD-SCID mice (panel B). NRS (normal rabbit serum) and PBS were used as controls.

As shown in FIG. 6, immune competent BALB/c and immune deficient NOD-SCID, which received aliquots of antiserum against Hyal-2 via tail veins, became protected against the growth of skin melanoma B16F10 cells.

Figure 7:
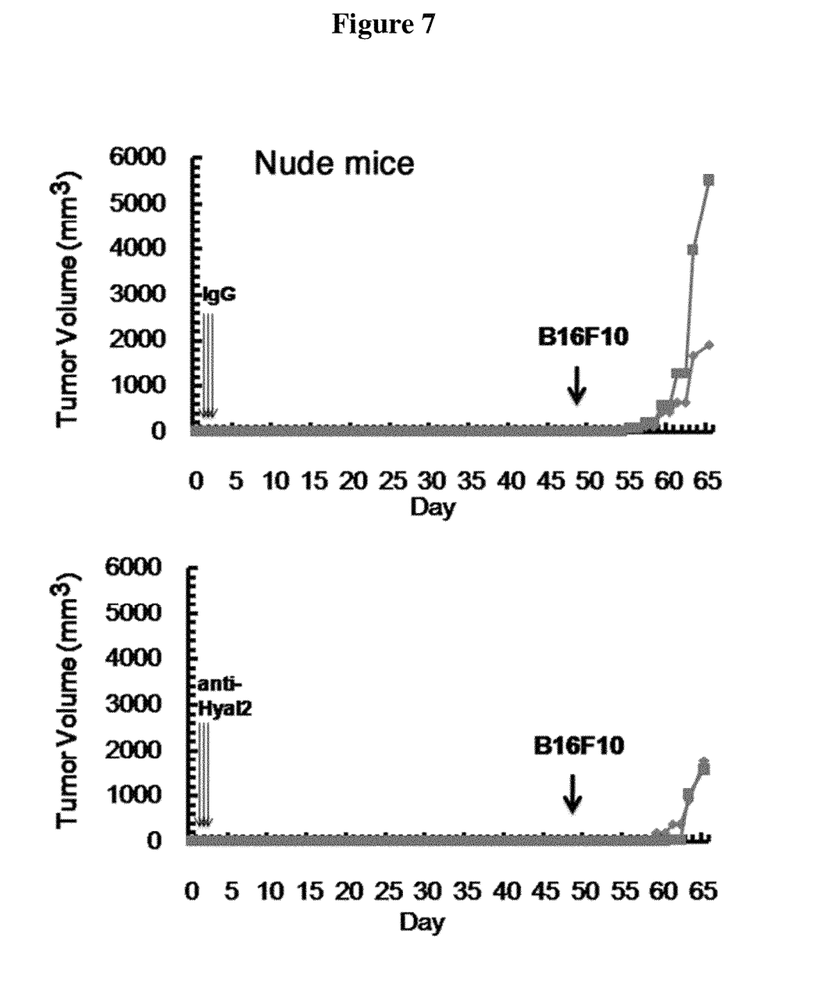
FIG. 7 is a graph showing the effect of anti-Hyal-2 antibody in suppressing B16F10 melanoma cell growth in nude mice.

In a similar experiment, nude mice were injected with an aliquot of Hyal-2 antiserum (10 µl with 90 µl PBS) or 2 µg normal rabbit serum IgG (in 100 µl PBS) in 3 consecutive days. A week later, mice were subcutaneously injected with B16F10 cells (2 million cells in each flank). Tumor sizes were measured daily. The results thus obtained show that Hyal-2 antibody also blocked B16F10 melanoma cell growth in nude mice. See FIG. 7.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for suppressing cancer cell growth, comprising contacting cancer cells with a composition comprising depolymerized hyaluronan, wherein the depolymerized hyaluronan comprises inter-chain covalent crosslinks, wherein at least about 90% of the depolymerized hyaluronan has a molecular weight ranging from about 100-500 kDa, and wherein the depolymerized hyaluronan is prepared by sonication of high molecular weight hyaluronan.

2. The method of claim 1, wherein the level of inter-chain covalent crosslinks is at least at 25% in the depolymerized hyaluronan.

3. The method of claim 1, wherein the sonication is carried out at about 20-80 kHz for about 3-6 hours.

4. The method of claim 3, wherein the sonication is carried out under a temperature ranging from about 50-80° C.

5. The method of claim 1, wherein the cancer cells are selected from the group consisting of breast cancer cells, melanoma cells, skin basal cell carcinoma cells, prostate cancer cells, lung cancer cells, glioblastoma cells, and neuroblastoma cells.

6. A method for treating cancer, comprising administering to a subject in need thereof an effective amount of a pharmaceutical composition, which comprises depolymerized hyaluronan and a pharmaceutically acceptable carrier, wherein the depolymerized hyaluronan comprises inter-chain covalent crosslinks, wherein at least about 90% of the depolymerized hyaluronan has a molecular weight ranging from about 100-500 kDa, and wherein the depolymerized hyaluronan is prepared by sonication of high molecular weight hyaluronan.

7. The method of claim 6, wherein the level of inter-chain covalent crosslinks is at least about 25% in the depolymerized hyaluronan.

8. The method of claim 6, wherein the sonication is carried out at about 20-80 kHz for about 3-6 hours.

9. The method of claim 8, wherein the sonication is carried out under a temperature ranging from about 50-80° C.

10. The method claim 6, wherein the subject is diagnosed with cancer.

11. The method of claim 6, wherein the subject is suspected of having cancer or at risk for cancer.

12. The method of claim 11, wherein the cancer is selected from the group consisting of breast cancer, melanoma, skin basal cell carcinoma, prostate cancer, lung cancer, glioblastoma, and neuroblastoma.

* * * * *